United States Patent

Reinehr et al.

Patent Number: 5,488,112
Date of Patent: Jan. 30, 1996

[54] DIMERIC BENZOTRIAZOLES AS UV ABSORBERS

[75] Inventors: Dieter Reinehr, Kandern, Germany; Jean-Pierre Bacher, Buschwiller; André Schmitter, Hegenheim, both of France

[73] Assignee: Ciba-Geigy Corporation, Tarrytown, N.Y.

[21] Appl. No.: 392,638

[22] Filed: Feb. 22, 1995

[30] Foreign Application Priority Data

Feb. 24, 1994 [CH] Switzerland .................. 554/94

[51] Int. Cl.$^6$ .................. C07D 403/14; C07D 249/20
[52] U.S. Cl. .................. 548/261; 540/460; 540/492; 544/318; 548/259
[58] Field of Search .................. 540/460, 492; 544/318; 548/259, 261

[56] References Cited

U.S. PATENT DOCUMENTS

| | | | |
|---|---|---|---|
| 3,399,173 | 8/1968 | Heller et al. | 260/47 |
| 3,629,192 | 12/1971 | Heller et al. | 260/45.8 |
| 4,077,971 | 3/1978 | Fujita et al. | 260/308 |
| 4,681,905 | 7/1987 | Kubota et al. | 524/91 |
| 4,812,498 | 3/1989 | Nakahara et al. | 524/91 |
| 4,859,726 | 8/1989 | Wang et al. | 524/91 |
| 4,948,666 | 8/1990 | Paul et al. | 428/334 |
| 5,233,047 | 8/1993 | MacLeay et al. | 548/260 |

FOREIGN PATENT DOCUMENTS

| | | |
|---|---|---|
| 2536335 | 2/1976 | Germany . |
| 408033 | 9/1966 | Switzerland . |
| 410851 | 10/1966 | Switzerland . |
| 497919 | 12/1970 | Switzerland . |
| 1169859 | 11/1969 | United Kingdom . |

OTHER PUBLICATIONS

Chemical Abstract 77062g of Swiss 497,919 (1971).
Chemical Abstract 86567n of Swiss 410,851 (1967).

Primary Examiner—Patricia L. Morris
Attorney, Agent, or Firm—Michele A. Kovaleski

[57] ABSTRACT

The invention relates to dimeric 2-(2'-hydroxyphenyl)benzotriazoles of the formula I

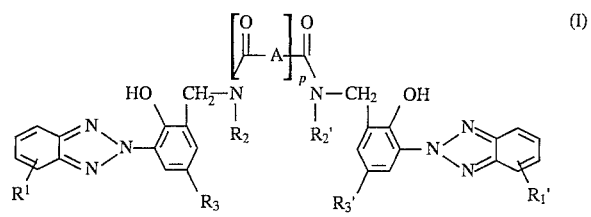

in which p is 0 or 1;

is $C_1$–$C_{12}$alkylene;

$R_1$ and $R'_1$, independently of one another, are hydrogen, halogen, $C_1$–$C_{18}$aklyl, $C_1$–$C_{18}$alkoxy or —CN;

$R_2$ and $R'_2$, independently of one another, are hydrogen or $C_1$–$C_{18}$alkyl or together are $C_2$–$C_{12}$alkylene or $C_2$–$C_{12}$hydroxyalkylene; and $R_3$ and $R'_3$, independently of one another, are hydrogen, halogen, $C_1$–$C_{18}$alkyl or $C_1$–$C_{18}$alkoxy.

The compounds of formula I are highly suitable for the stabilization of organic material against the harmful effects of heat, oxygen and light, in particular UV radiation.

5 Claims, No Drawings

DIMERIC BENZOTRIAZOLES AS UV ABSORBERS

The invention relates to novel dimeric 2-(2'-hydroxyphenyl)benzotriazoles, to their use as stabilizers for organic polymers, to corresponding stabilized compositions, and to a process for the stabilization of organic polymers.

Certain 2-(2'-hydroxyphenyl)benzotriazoles have been used for some time as stabilizers for organic polymers. The use of some dimeric compounds of this type has also been described. For example, some methylene-bridged bisbenzotriazoles are disclosed, for example, in U.S. Pat. Nos. 4,812,498, 4,948,666 and 4,681,905; 4,859,726 describes 2-(2'-hydroxyphenyl)benzotriazoles which are chemically bonded to one another in the 3'-position via diisopropylidenebenzene.

U.S. Pat. Nos. 4,077,971, GB-A-1 169 859 and CH-A-408 033 describe some 2-(2'-hydroxyphenyl)benzotriazoles which carry a substituent of the —$CH_2$—N(R)—CO—R type, where each R is a certain organic radical, in the 3'-position and which can likewise be employed as light stabilizers.

There continues to be a demand for dimeric benzotriazole UV absorbers.

The invention relates to novel dimeric benzotriazoles which are surprisingly suitable for the stabilization of organic polymers against the harmful effect of heat, oxygen and light, in particular UV radiation.

The invention therefore relates to compounds of the formula I

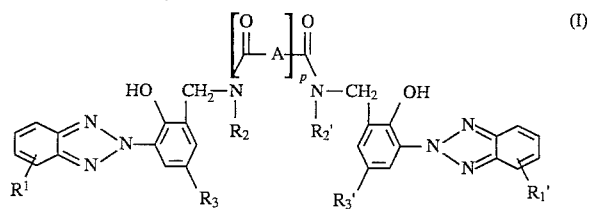

in which p is 0 or 1;

A is $C_1$–$C_{12}$alkylene;

$R_1$ and $R'_1$, independently of one another, are hydrogen, halogen, $C_1$–$C_{18}$alkyl, $C_1$–$C_{18}$alkoxy or —CN;

$R_2$ and $R'_2$, independently of one another, are hydrogen or $C_1$–$C_{18}$alkyl or together are $C_2$–$C_{12}$alkylene or $C_2$–$C_{12}$hydroxyalkylene; and $R_3$ and $R'_3$, independently of one another, are hydrogen, halogen, $C_1$–$C_{18}$alkyl or $C_1$–$C_{18}$alkoxy.

Particular mention should be made of the extraordinarily high sublimation resistance of the compounds of the formula I and their good resistance to extraction.

Compounds of the formula I in which p is 0 are preferred.

Preference is furthermore given to compounds of the formula I in which $R_1$ and $R'_1$, independently of one another, are hydrogen, halogen, $C_1$–$C_{12}$alkyl, $C_1$–$C_{12}$alkoxy or —CN;

$R_2$ and $R'_2$, independently of one another, are hydrogen or $C_1$–$C_{12}$alkyl or together are $C_2$–$C_3$alkylene or $C_2$–$C_3$hydroxyalkylene; and $R_3$ and $R'_3$, independently of one another, are hydrogen, chlorine, $C_1$–$C_{12}$alkyl or $C_1$–$C_{12}$alkoxy.

Of outstanding interest are compounds of the formula I in which p is 0 and $R_1$ and $R'_1$ are identical and are hydrogen, $C_1$–$C_4$alkoxy or chlorine;

$R_2$ and $R'_2$ are identical and are hydrogen or $C_1$–$C_4$alkyl or together are $C_2$–$C_3$alkylene or $C_2$–$C_3$hydroxyalkylene; and $R_3$ and $R'_3$ are identical and are $C_1$–$C_9$alkyl or $C_1$–$C_4$alkoxy;

in particular compounds of the formula I in which p is 0 and $R_1$ and $R'_3$ are identical and are hydrogen or chlorine;

$R_2$ and $R'_2$ are identical and are hydrogen or methyl, or $R_2$ and $R'_2$ together are ethylene or 1,2-dihydroxyethylene; and $R_3$ and $R'_3$ are identical and are $C_1$–$C_9$alkyl.

Halogen is —F, —Cl, —Br or —I; in all embodiments of the invention, one halogen substituent is preferably —Cl or —Br, especially —Cl.

Alkylene A is methylene, ethylene, propylene, butylene, pentylene, hexylene, heptylene, octylene, nonylene, decylene, undecylene or dodecylene. Preference is given to $C_1$–$C_8$alkylene, in particular straight-chain $C_1$–$C_8$alkylene.

Alkyl $R_1$, $R'_1$, $R_2$, $R'_2$, $R_3$ and $R'_3$ are, independently of one another and within the confines of their definitions above, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl or octadecyl; preference is given to $C_1$–$C_{12}$alkyl, especially $C_1$–$C_9$alkyl. Alkyl $R_1$, $R'_1$, $R_2$ and $R'_2$ are, independently of one another, preferably $C_1$–$C_4$alkyl, especially methyl.

Alkyl $R_3$ and $R'_3$ are preferably, independently of one another, either methyl or branched $C_4$–$C_{12}$alkyl, in particular methyl or tertiary $C_4$–$C_8$alkyl. A tertiary alkyl group here denotes a saturated aliphatic hydrocarbon radical whose bonding carbon atom is itself bonded to 3 further carbon atoms. Examples of tertiary $C_4$–$C_8$alkyl include tert-butyl (1,1-dimethylethyl) and tert-octyl (1,1,3,3-tetramethylbutyl).

$R_1$ and $R'_1$, and $R_3$ and $R'_3$ are preferably in each case identical radicals. $R_2$ and $R'_2$ are also identical radicals so long as they are not together alkylene or hydroxyalkylene.

If $R_2$ and $R'_2$ together are alkylene or hydroxyalkylene, p is generally 0; $R_2$ and $R'_2$ then form, preferably together with the urea unit to which they are bonded, a five-membered or six-membered ring, especially a 5-membered ring. The ring can be substituted by alkyl or, if $R_2$ and $R'_2$ together are hydroxyalkylene, additionally by one or more —OH groups. Alkylene or hydroxyalkylene $R_2$ and $R'_2$ together are particularly preferably 1,2-ethylene, 1,3-propylene, 1,2-ethylene which is substituted by 1 or 2 —OH groups or 1,3-propylene which is substituted by 1 or 2 —OH groups, especially 1,2-ethylene or 1,2-ethylene which is substituted by 1 or 2 —OH groups.

The novel compounds can be prepared analogously to the processes described in U.S. Pat. No. 4,077,971, GB-A-1 169 859 or U.S. Pat. No. 3,629,192. They are expediently prepared by reacting one equivalent of a benzotriazole of the formula II

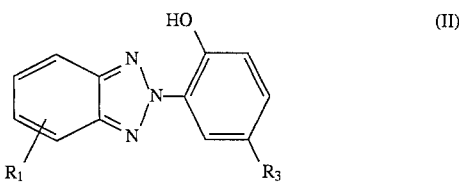

and one equivalent of a benzotriazole of the formula II'

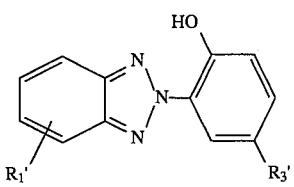

with one equivalent of a compound of the formula III

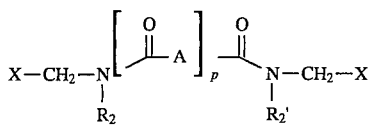

where A, $R_1$, $R'_1$, $R_2$, $R'_2$, $R_3$, $R'_3$ and p are as defined above for the formula I, and X is OH, halogen or alkoxy. The reaction temperature is not crucial and can be, for example, from $-10°$ C. to $+150°$ C.; the reaction is expediently carried out in a suitable reaction medium (for example in an acid or an organic solvent) in the presence of a suitable additive (for example an acid, an alkali metal compound or a dehydrating agent), it being possible for the reaction medium and the additive to be identical.

Preference is given to compounds of the formula III in which X is hydroxyl or chlorine, in particular hydroxyl.

A novel compound of the formula I can be prepared by reacting, for example, compounds of the formulae II and II', which are identical or different, with the compound of the formula III in concentrated sulfuric acid, for example containing 80–100% of $H_2SO_4$, in a mixture of acetic anhydride and glacial acetic acid, in polyphosphoric acid (phosphorus content from about 100 to 130%, based on orthophosphoric acid), or in an inert solvent, for example toluene or hexane, with addition of a dehydrating agent, for example p-toluenesulfonic acid or aluminium chloride, expediently with stirring. Preference is given to sulfuric acid, and the reaction is preferably carried out at from $-5°$ C. to $+40°$ C., the temperature of the reaction mixture preferably being kept in the range from $0°$ C. to $30°$ C., especially from $15°$ C. to $25°$ C. (room temperature) after all the components have been metered in. The product can be worked up and isolated in a known manner, for example by dilution with water, expediently with cooling (ice water), and removal of the solid product by filtration followed by washing and drying.

Examples of methylol compounds of the formula III which can be used include N,N'-dimethylolurea, N,N'-dimethylol-N,N'-dimethylurea, 1,3-dimethylol-tetrahydroimidazol-2-one (=1,3-dimethylol-ethyleneurea), 1,3-dimethylol-4,5-dihydroxy-tetrahydroimidazol-2-one, N,N'-dimethylol-sebacamide, N,N'-dimethylol-malonamide and N,N'-dimethylol-succinamide.

The compounds of the formula I can also be prepared by reacting compounds of the above formulae II and II' with a compound of the formula IV

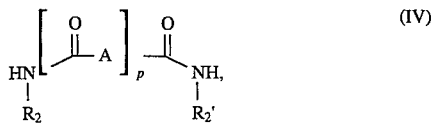

at from $0°$ to $50°$ C. in sulfuric acid in the presence of formaldehyde, analogously to a process described in U.S. Pat. No. 4,077,971. Details on carrying out the reaction are given in this publication.

The novel compounds of the formula I are highly suitable for the stabilization of organic materials, in particular organic polymers, against the harmful effects of heat, oxygen and light, in particular UV radiation. Examples of such organic materials are listed below.

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the tree form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

The invention therefore also relates to a composition comprising:

A) an organic material which is sensitive to damage by light, oxygen and/or heat, in particular an organic polymer, and B) a compound of the formula I as stabilizer.

The novel compounds of the formula I can particularly advantageously be employed in compositions comprising, as component A, an organic polymer, for example a synthetic organic polymer. The compounds of the formula I are particularly important for the stabilization of compositions comprising a thermoplastic polymer.

The novel compositions can be a constituent of a coating composition, for example of a paint, or of a plastic composition.

Preference is given to compositions in which component A is i) a thermoplastic polymer selected from organic polymers containing hetero atoms, in particular nitrogen and/or oxygen, in the main chain, styrene copolymers, styrene graft polymers and polymethyl methacrylates (PMMA); or ii) a paint binder.

Thermoplastic polymers containing hetero atoms in the main chain are, in particular, O-, S- and N-containing polymers. Examples thereof are listed above under points 13 to 20. Of these, preference is given to polycarbonates, polyesters, polyamides, polyacetals, polyphenylene oxides and polyphenylene sulfides, in particular polycarbonates, polyesters, for example polyethylene terephthalate (PET), and polyamides (PA), for example PA 6 and PA 6/6, but especially polycarbonates.

Examples of styrene copolymers and styrene graft polymers are listed above under points 6 and 7.

The paint binders can comprise at least one of the polymers listed above. Examples of paints containing specific binders are the following:

1. paints based on low- or high-temperature-crosslinkable alkyd, acrylate, polyester, epoxy or melamine resins, or mixtures of such resins, if desired with addition of a curing catalyst;

2. two-component polyurethane paints based on hydroxyl-containing acrylate, polyester or polyether resins and aliphatic or aromatic isocyanates, isocyanurates or polyisocyanates;

3. one-component polyurethane paints based on block isocyanates, isocyanurates or polyisocyanates which are deblocked during baking;

4. two-component paints based on (poly)ketimines and aliphatic or aromatic isocyanates, isocyanurates or polyisocyanates;

5. two-component paints based on (poly)ketimines and an unsaturated acrylate resin or a polyacetoacetate resin or a methyl methacrylamidoglycolate;

6. two-component paints based on carboxyl- or amino-containing polyacrylates and polyepoxides;

7. two-component paints based on anhydride group-containing acrylate resins and a polyhydroxyl or polyamino component;

8. two-component paints based on (poly)oxazolines and anhydride group-containing acrylate resins or unsaturated acrylate resins or aliphatic or aromatic isocyanates, isocyanurates or polyisocyanates;

9. two-component paints based on unsaturated polyacrylates and polymalonates;

10. thermoplastic polyacrylate paints based on thermoplastic acrylate resins or non-self-crosslinking acrylate resins in combination with etherified melamine resins;

11. paint systems based on siloxane-modified acrylate resins;

12. paint systems based on fluorine-modified acrylate resins, and 13. paint systems based on allyl glycidyl ethers.

The paints can be applied as one- or two-coat finishes, the novel stabilizers preferably being added to the unpigmented top coat.

The paints can be applied to the substrates (metal, plastic, wood, etc) by conventional methods, for example by brushing, spraying, pouring, dipping or electrophoresis.

A preferred embodiment of the present invention thus comprises paints or coatings (for example automotive finishes) comprising at least one novel compound. Suitable binders are, for example, those mentioned above.

The invention thus also relates to a process for the stabilization of organic material, in particular organic polymers, against damage by light, oxygen and/or heat, which comprises adding a compound of the formula I as stabilizer to the organic material, and to the use of compounds of the formula I for the stabilization of organic material.

The amount of stabilizer to be used depends on the organic material to be stabilized and on the intended use of the stabilized material. In general, the novel composition comprises from 0.01 to 15 parts by weight, in particular from 0.1 to 5 parts by weight, of the stabilizer (component B) per 100 pans by weight of component A.

The novel compounds and, if desired, further additives can be incorporated into the organic polymers by, for example, the mixing methods conventional in industry. The incorporation can be carried out before or during shaping, for example by mixing the pulverulent components, or by addition of the stabilizer to the melt or solution of the polymer, or by application of the dissolved or dispersed compounds to the polymer, if necessary with subsequent evaporation of the solvent. Elastomers can also be stabilized as latices. Another method of incorporating the novel compounds into polymers comprises adding them before or during polymerization of the corresponding monomers or before crosslinking.

The novel compounds or mixtures thereof can also be added to the plastics to be stabilized in the form of a masterbatch, which comprises these compounds, for example, in a concentration of from 2.5 to 25% by weight.

The novel compounds can expediently be incorporated by the following methods:

as an emulsion or dispersion (for example to latices or emulsion polymers), as a dry mix during the mixing of additional components or polymer mixtures, by direct addition into the processing apparatus (for example extruder, internal mixer, etc)

as a solution or melt.

The stabilized polymer compositions obtained in this way can be converted into shaped articles, for example into fibres, films, tapes, sheets, multiwall sheets, containers, pipes and other profiles, by conventional methods, for example by hot pressing, spinning, extrusion or injection moulding.

The invention therefore furthermore relates to the use of the novel polymer composition for the production of a shaped article.

Also of interest is the use in multilayer systems, where a novel polymer composition having a relatively high content of stabilizer of the formula Ib, for example 5–15% by weight, is applied in a thin film (10–100 µm) to a shaped article made from a polymer containing little or no stabilizer of the formula Ib. The application can be carried out at the same time as the shaping of the base article, for example by coextrusion. However, the application can also be carried out to the base article in its finished shape, for example by lamination with a film or by coating with a solution. The outer layer or layers of the finished article have the function of a UV filter which protects the interior of the article against UV light. The outer layer preferably contains 5–15% by weight, in particular 5–10% by weight, of at least one stabilizer of the formula Ib.

The use of the novel polymer composition for the production of multilayer systems, where the outer layer(s) in a thickness of 10–100 μm comprise a novel polymer composition, while the inner layer contains little or no stabilizer of the formula Ib, therefore represents a further subject-matter of the invention.

The polymers stabilized in this way are distinguished by high weathering resistance, in particular by high resistance to UV light. They thus retain their mechanical properties and their colour and gloss for a long time, even when used outside.

The stabilizer (component B) can also be a mixture of two or more novel compounds. In addition to the stabilizer of the formula I, the novel compositions, stabilized coating materials or organic polymers can also contain other stabilizers and/or other additives, for example antioxidants, further light stabilizers, metal deactivators, phosphites or phosphonites. Examples thereof are the following stabilizers:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6 -dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1' -methylundec-1'-yl)phenol, 2,4-dimethyl-6-(1'-methylheptadec-1'-yl)phenol, 2,4-dimethyl-6-(1'-methyltridec-1 '-yl)phenol, and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4 -nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6 -tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α -methylcyclohexyl)phenol], 2,2'-methylenebis(4-methyl-6-cyclohexylphenol), 2,2'-methylenebis(6-nonyl-4 -methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α -methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenol)butane, 2,6-bis(3-tert-butyl-5-methyl-2 -hydroxybenzyl )-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2 -methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3 -tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6 -trimethylbenzene, 1,4-bis(3,5-di-tert-butyl-4-hydroxybenzyl)-2, 3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)- 1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4 -hydroxybenzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-Iris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4 -hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2' -hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2' -hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3', 5'-di-tert-amyl-2' -hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5 -chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]- 2H-benzotriazole with polyethylene glycol 300; [R—$CH_2CH_2$—COO($CH_2$)$_3$]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-ββ-diphenylacrylate, isooctyl α-cyano-ββ-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, his(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4- piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2 -(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butyl-amino-2,2,6,6 -tetramethylpiperidyl)-1,3,5-triazine and 1,2-bis(3-aminopropylamino)ethane, the condensate of 2-chloro-4,6-di-(4-n-butylamino-1, 2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8 -triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyoxanilide, 2,2'-dioctyloxy-5,5' -di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5 -triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2- hydroxy- 4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5 -triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,5-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,5-tris(tert-butylphenyl)pentaerythritol diphsophite, tristearyl sorbitol triphosphite, tetrakis(2,4-di-tert-butylphenyl) 4,4'-biphenylene diphosphonite, 5-isooctyloxy- 2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1, 3,2-dioxaphosphocin, bis(2,4-di-tert-butyl-6-methylphenyl) methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244, 5,175,312, 5,216,052, 5,252,643, 4,316,611, 4,316,622, 4,316,876, EP-A-0 589 839 or EP-A-0 59 1102 or 3-[4-(2-acetoxyethoxy)phenyl]-5,7 -di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl) benzofuran-2-one]. 5,7-di-tert-butyl-3-(4-ethoxyphenyl) benzofuran-2-one, 3-(4-acetoxy-3,5-dimethylphenyl)-5,7 -di-tert-butyl-benzofuran-2-one, 3-(3,5-dimethyl-4-pivaloyloxyphenyl)-5,7-di-tert-butyl-benzofuran-2-one.

The type and amount of the other stabilizers added are determined by the type of the substrate to be stabilized and by its intended application; frequently, from 0.1 to 5% by weight, based on the polymer to be stabilized, are used.

The examples below describe the novel coating materials in greater detail, without restricting the invention thereto. Parts are by weight, and % are % by weight.

EXAMPLE 1

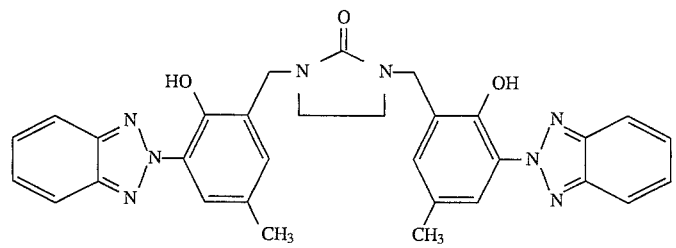

45 g (0.2 mol) of 2-(2'-hydroxy-5'-methyl)benzotriazole are introduced into 200 ml of concentrated sulfuric acid at from 0° to −5° C. 29.2 g (0.1 mol) of 1,3-dimethylolethyleneurea (50% solution in water) are then added dropwise over the course of 20 minutes at from −5° to 0° C. The mixture is subsequently stirred at +20° C. for 2 hours, poured into 1 l of ice water and filtered, and the filter cake is washed with water until neutral. The solid is stirred with 600 ml of dimethylacetamide, warmed to 100° C., cooled and then filtered off. Washing with dimethylacetamide and water followed by drying at 100° C. in a vacuum drying cabinet gives 42 g of a white powder of melting point 283.5° C., corresponding to a yield of 74.9%.

EXAMPLE 2

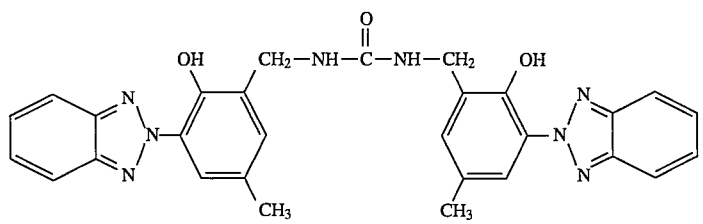

The procedure is as described in Example 1, but 12 g (0.1 mol) of bismethylolurea are used instead of the 1,3-dimethylolethyleneurea. 52 g of a white product of melting point 310.4° C., corresponding to a yield of 97.3%, are obtained.

EXAMPLE 3

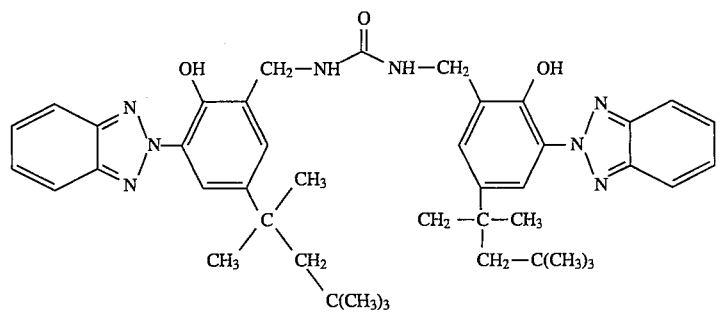

The procedure is as described in Example 2, but 64.6 g (0.2 mol) of 2-(2'-hydroxy-5'-tert-octyl)benzotriazole are used instead of 45 g (0.2 mol) of 2-(2'-hydroxy-5'-methyl-)benzotriazole. Work-up gives 21.5 g of a white product of melting point 190° C.

EXAMPLES 4–6

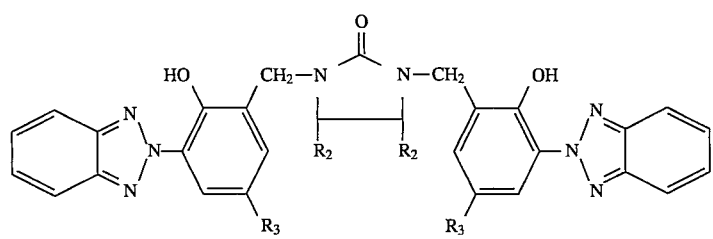

Compound Nos. 4–6 of the general formula shown above were prepared by the method described in Example 1. The structure and physical data for these compounds are shown in the table below.

TABLE

| Compounds of Examples 4–6 | | | |
|---|---|---|---|
| Example No. | $R_3$ | $R_2$ | Melting point |
| 4 | tert-octyl | H | 174.6° C. |
| 5 | tert-octyl | OH | 215° C. |
| 6 | methyl | OH | 338° C. |

Use Examples

EXAMPLE 7

Stabilization of polycarbonate (PC)

10 g of polycarbonate powder (Lexan® 115) are dissolved in 50 g of methylene chloride at room temperature with stirring, which requires several hours. 0.2 g of the UV absorber from Example 4 or 5, corresponding to addition of 2% of additive, are added. For comparative purposes, another solution is prepared without UV absorber. Films having a thickness of 20 μm are cast from these solutions.

The films are exposed in an Atlas CI 65 Weatherometer at a black-panel temperature of 63° C. and a relative humidity of 60%. Before commencement of the weathering and at regular intervals thereafter, the discolouration of the samples is checked by measuring the Yellowness Index (YI, method ASTM D 1925). The samples are also analysed for brittleness. The results are shown in Table 1; YI(0) denotes the initial colour (= Yellowness Index before commencement of weathering), and embrittlement of the sample is marked by the symbol*.

TABLE 1

Yellowness Index YI and embrittlement before and during weathering; samples according to the invention containing 2% of UV absorber

| UV absorber | Weathering duration/h | | | | | | | | |
|---|---|---|---|---|---|---|---|---|---|
| | 0 | 552 | 1046 | 1548 | 2030 | 3000 | 3501 | 4502 | 5507 |
| None | 0.1 | 3.6 | 12.2* | | | | | | |
| Example 4 | 0.2 | 1.6 | 3.0 | 9.2 | 9.3 | 10.8 | 12.1 | 12.2 | 12.9* |
| Example 5 | 0.5 | | | | | | | | |

*Embrittlement of the sample

The data reproduced in Table 1 show that admixture of the novel compounds results in virtually no discolouration of the polycarbonate. In the weathering test, the novel compounds exhibit excellent effectiveness.

EXAMPLE 8

Stabilization of polymethyl methacrylate (PMMA)

15 g of polymethyl methacrylate and 60 mg or 300 mg of the novel stabilizer (corresponding to 0.4% or 2% respectively of stabilizer) are dissolved in 85 g of methylene chloride at room temperature. From this solution, films having a thickness of 30 μm after evaporation of the solvent and after drying in vacuo are drawn on glass plates.

The films are peeled off from the glass plates and tensioned in cardboard flames (6×3 cm). The samples are irradiated for 3 months in a UV exposure unit with 5 TL/09 fluorescent lamps and 5 TL/12 lamps mounted 20 cm above the samples. The UV absorption is measured at regular intervals at the wavelength of maximum absorbence. In addition, the discolouration of the samples is checked by measurement of the Yellowness Index (YI, method ASTM D 1925).

The samples stabilized in accordance with the invention have excellent light stability.

What is claimed is:

1. A compound of the formula I

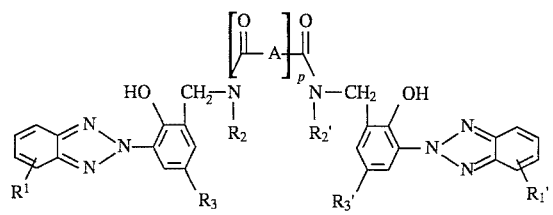

in which p is 0 or 1;

A is $C_1$–$C_{12}$alkylene;

$R_1$ and $R'_1$, independently of one another, are hydrogen, halogen, $C_1$–$C_{18}$alkyl, $C_1$–$C_{18}$alkoxy or —CN;

$R_2$ and $R'_2$, independently of one another, are hydrogen or $C_1$–$C_{18}$alkyl or together are $C_2$–$C_{12}$alkylene or $C_2$–$C_{12}$hydroxyalkylene; and $R_3$ and $R'_3$, independently of one another, are hydrogen, halogen, $C_1$–$C_{18}$alkyl or $C_1$–$C_{18}$alkoxy.

2. A compound of the formula I according to claim 1, in which p is 0.

3. A compound of the formula I according to claim 1, in which $R_1$ and $R'_1$, independently of one another, are hydrogen, halogen, $C_1$–$C_{12}$alkyl, $C_1$–$C_{12}$alkoxy or —CN;

$R_2$ and $R'_2$, independently of one another, are hydrogen or $C_1$–$C_{12}$alkyl or together are $C_2$–$C_3$alkylene or $C_2$–$C_3$hydroxyalkylene; and $R_3$ and $R'_3$, independently of one another, are hydrogen, chlorine, $C_1$–$C_{12}$alkyl or $C_1$–$C_{12}$alkoxy.

4. A compound of the formula I according to claim 1, in which p is 0 and $R_1$ and $R'_1$ are identical and are hydrogen, $C_1$–$C_4$alkoxy or chlorine;

$R_2$ and $R'_2$ are identical and are hydrogen or $C_1$–$C_4$alkyl or together are $C_2$–$C_3$alkylene or $C_2$–$C_3$hydroxyalkylene; and $R_3$ and $R'_3$ are identical and are $C_1$–$C_9$alkyl or $C_1$–$C_4$alkoxy.

5. A compound of the formula I according to claim 1, in which p is 0 and $R_1$ and $R'_1$ are identical and are hydrogen or chlorine;

$R_2$ and $R'_2$ are identical and are hydrogen or methyl, or $R_2$ and $R'_2$ together are ethylene or 1,2-dihydroxyethylene; and $R_3$ and $R'_3$ are identical and are $C_1$–$C_9$alkyl.

* * * * *